Figure 1:
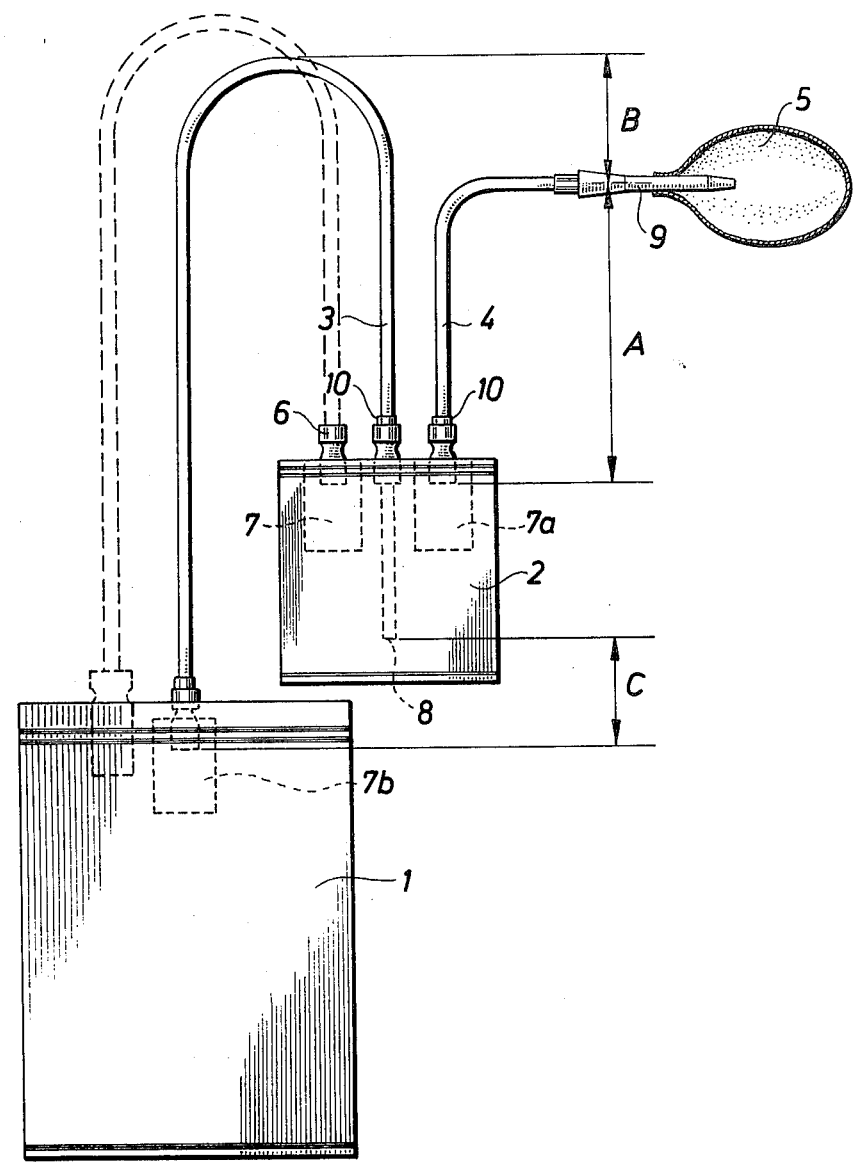

United States Patent [19]

Jarund

[11] 4,084,593

[45] Apr. 18, 1978

[54] BLADDER TRAINING APPARATUS

[75] Inventor: Harry Sigurd Valdemar Järund, Lund, Sweden

[73] Assignee: Jarund Devello AB, Fjallbacka, Sweden

[21] Appl. No.: 676,144

[22] Filed: Apr. 12, 1976

[30] Foreign Application Priority Data

Apr. 15, 1975 Sweden .................................. 7504312
Jul. 16, 1975 Sweden .................................. 7508120

[51] Int. Cl.² .............................................. A61F 5/44
[52] U.S. Cl. .................................... 128/295; 128/2 F; 128/227; 128/DIG. 25
[58] Field of Search ............................... 128/275–278, 128/294, 295, 227, 228, 2 F, 349 R, DIG. 24, DIG. 25; 4/110; 73/440–442; 229/62.5; 150/9

[56] References Cited

U.S. PATENT DOCUMENTS

| 2,602,448 | 7/1952 | McKenna | 128/227 |
| 2,804,257 | 8/1957 | Hasler et al. | 229/62.5 |
| 2,860,636 | 11/1958 | Seitchik et al. | 128/227 |
| 3,503,401 | 3/1970 | Andersen et al. | 128/349 R |

Primary Examiner—John D. Yasko
Assistant Examiner—Henry S. Layton

[57] ABSTRACT

Apparatus for use in training the bladder of an incontinent patient including a pressure chamber connectable to the bladder with a catheter and a collecting container connected to the pressure chamber by a narrow tube. The pressure chamber is to be lower than the bladder and the collecting container is below the pressure chamber, while the tube extends upwardly from the pressure chamber. In use, the pressure chamber fills up, pressurizing the bladder, until urine reaches the highest part of the tube whereon the pressure chamber and bladder are emptied and the pressure reduced.

13 Claims, 2 Drawing Figures

BLADDER TRAINING APPARATUS

The present invention relates to apparatus for use in training the bladders of patients suffering from urine incontinence.

There are many patients who suffer from urine incontinence, and it is normal practice for the urine to be drawn off continuously through a catheter in permanent communication with the urine bladder and connected to a collecting container, such as a plastic bag, placed at a lower level than the bladder. However, the level difference between bladder and bag gives rise to a certain amount of partial vacuum in the bladder and the system as such gives rise to a suction action. For many patients this may be injurious since all training of the bladder, that is to say its repeated expansion and contraction, is eliminated.

In order to solve this problem, i.e. to offer a chance of training the bladder at least to a certain extent, a method has sometimes been used in which the outlet tubes to the urine bag are closed off for certain periods of time. However, there are practical difficulties with such a solution since it must be attended to by already overworked personnel who cannot attend to the emptying in accordance with the individual bladder pressure for each patient. Attempts have also been made to use complicated electronic control systems for the purpose, but these have been found to be much too expensive for practical use. It has also been found that the manual bladder training method mentioned above, in which the flow from the bladder is interrupted at certain times, may result in urine escaping through the urethra on the outside of the catheter. When the bladder is emptied a corresponding low pressure occurs so that air is drawn in around the outside of the catheter, entailing an obvious risk of infection.

It is an aim of the invention to provide apparatus for use in bladder training in which the above problems are at least reduced.

According to the present invention there is provided apparatus for use in training the bladder of an incontinent patient including a pressure chamber to be located at a level below the bladder, a collecting container to be located at a level below the pressure chamber, a narrow tube to extend upwardly from a lower region of the pressure chamber and connecting the pressure chamber to this collecting container and an inlet to the pressure chamber which is connectable to the bladder whereby, in use, the pressure chamber fills up and the bladder is placed under increasing pressure until urine reaches the highest part of the tube whereon urine passes to the collecting container and the pressure chamber and bladder are emptied and pressure in the bladder reduced.

A further tube can be provided connected to the inlet and a catheter can be connected to the further tube.

Preferably, an air supply inlet is provided in the upper part of the pressure chamber to equalise the partial vacuum occurring after the emptying phase. This inlet may be connected by an air tube to the upper part of the urine bag or to a closed air bag. A one way valve is preferably provided in the air supply inlet, alternatively the air tube may be, in part, above the highest point of the narrow tube.

The invention offers the following advantages:
1. the forced rinsing or flushing of the system occurs at regular intervals, which prevents the collection of urine residue and bacteria growth which might result in the spread of infection to the bladder,
2. the bladder training provided by the apparatus counteracts any tendency towards a so-called "shrunken bladder," and atrophy of the muscles of the bladder wall; healthy bladder muscles being, of course, also less susceptible to infection,
3. due to the construction of the pressure chamber the emptying thereof will be interrupted so that an excessive partial vacuum in the bladder is prevented; this might otherwise cause air to be drawn into the bladder.

The invention will be more clearly understood from the following description which is given by way of example only with reference to the accompanying drawings, in which:

FIG. 1 is a schematical view of a first embodiment of the invention; and

Figure 2:
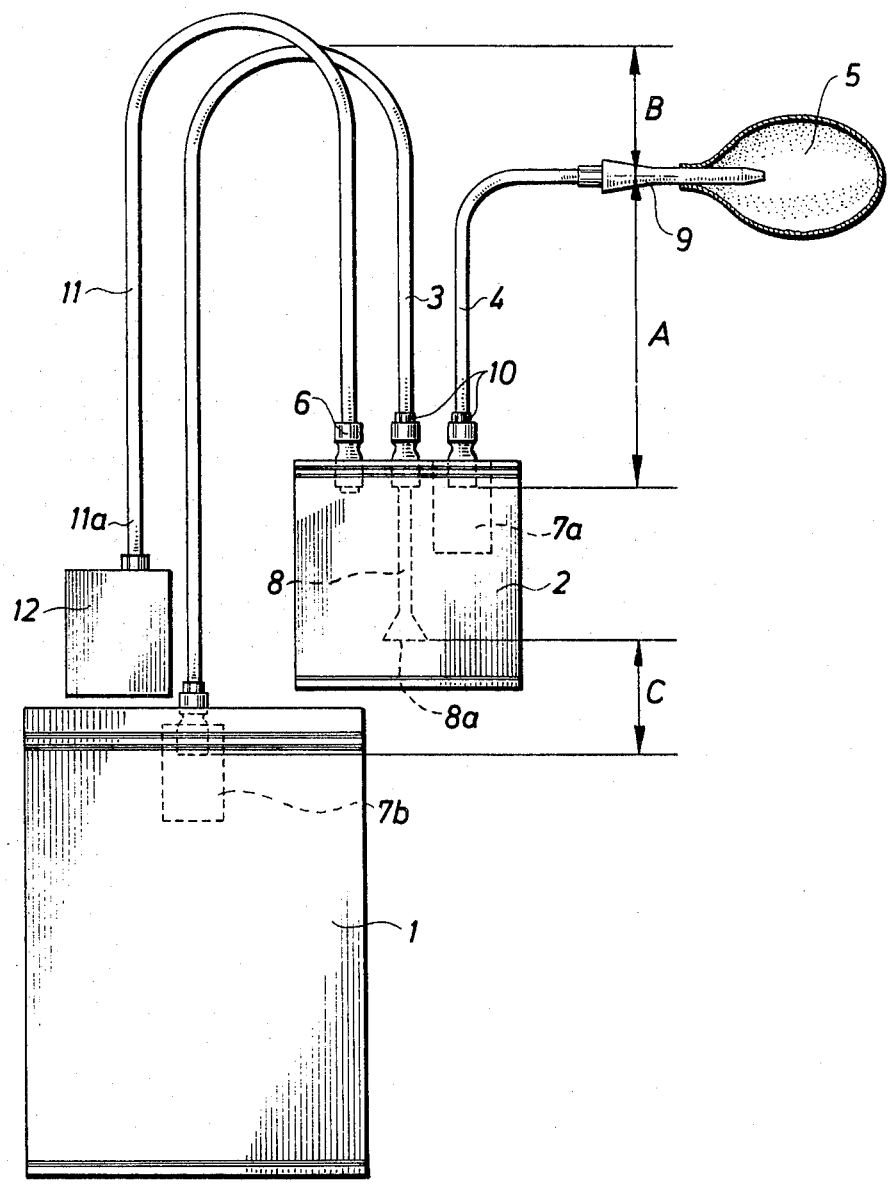

FIG. 2 a schematical view of a section embodiment of the invention.

FIG. 1 shows a schematical view of a first embodiment of apparatus of the invention when in use. The apparatus consists of three main components: a urine bag or collecting container 1, a pressure chamber 2 and a pipette or other narrow tube 3 extending upwardly from the pressure chamber. The pressure chamber 2 is connected to the urine bag 1 by the pipette 3 which is suitably in the form of a tube having its orifice 8 close to the bottom of the pressure chamber 2, and an inlet 10 of the pressure chamber 2 is connected by a further tube 4 to a bladder 5 via a catheter 9.

When in use the various components should be located in relation to each other in approximately the manner shown in the drawing, i.e. the level difference between the inlet of the pressure chamber 2 and the bladder 5 should be preferably be a distance such as suggested by dimension A, the level difference between the orifice of the pipette 3 in the pressure chamber 2 and the inlet to the urine bag 1 as suggested by the distance C, and the level difference between the highest point of the pipette 3 and the bladder 5 should suitably be as suggested by the distance B.

The pressure chamber 2 is also provided with an air supply inlet 6 provided with a non-return valve 7 inside the chamber 2, to permit air to flow into the chamber 2, but to prevent urine from leaking out through the valve. According to a further feature of the invention, this air inlet 6 may be by way of a tube to the upper part of the urine bag 1. Additional non-return valves 7a, 7b may also be provided at the orifices of tubes 4 and 3 in the pressure chamber 2 and urine bag 1, respectively.

The apparatus shown in FIG. 1 functions in the following manner:

The urine runs down from the bladder 5 to the pressure chamber 2 through the tube 4. The pressure chamber is thus gradually filled with urine which after a while starts to rise in the tube 3. This causes a gradual increase in pressure in the bladder 5 which thus expands and is refilled with urine. As the pressure increases in the bladder, the urine rises still further in the tube 3 and finally passes the highest point of the tube 3, then to flow down into the urine bag 1. A syphon action thus occurs in the tube 3 since the urine bag 1 is at a lower level than the pressure chamber 2. This syphon action will cause urine to be emptied both from the pressure chamber 2 and from the bladder 5, which will therefore be caused to contract. When the urine level in the pressure chamber 2 has fallen below the inlet 8 of the pipette, air will be drawn in to the tube 3, whereupon the syphon action is interrupted. A partial vacuum then developes in the pressure chamber 2 so that air is drawn in to the pressure chamber through the air inlet 6. The pressure chamber and bladder are then refilled and the process described above is automatically repeated.

In the events described above however, a small quantity of air is introduced through the valve 6 and this air will remain in the urine bag 1. This means that the urine bag cannot be completely filled with urine. However, this drawback can be eliminated by connecting the valve 6 to the urine bag by a tube so that the air necessary for the device to function will circulate within the system.

In an alternative embodiment shown in FIG. 2, the air inlet 6 is connected by a tube 11 to a separate air containing bag 12, rather than to bag 1. The highest point of the tube 11 is above the highest point of the pipette 3 and the pressure chamber 2 will therefore function slightly differently from that in the embodiment shown in FIG. 1. All air in the pressure chamber 2 will be pressed out through the tube 11, as the chamber fills up whereupon liquid from the pressure chamber 2 will also be pressed up into the tube 11 as it rises in tube 3. However, this liquid cannot rise further than the highest part of the pipette 3, and when the syphon action starts and the liquid is drawn into the urine bag 1 the liquid level in the pipe 11 quickly drops and air from the air bag 12 is drawn down into the pressure chamber 2.

Of course, the end 11a of the tube 11 need not necessarily open into a bag 12, but the use of a closed system is preferred so that the air from the pressure chamber shall not escape into the surrounding air.

Either embodiment of apparatus can easily be adjusted to satisfy the bladder training requirements of various patients by altering the levels A and B in suitable manner. The partial vacuum which occurs is determined by the level A and the over-pressure by the level B.

In order to prevent reverse flow of the urine with the inherent risk of spreading bacteria, the connection between pressure chamber and tube to the bladder may be provided with a non-return valve.

The coupling by which the tube 3 is connected to the urine bag is preferably manufactured in the following manner:

Before the top bag opening is sealed by welding, a connecting member is placed in the bag opening, the outside of the connecting member where it passes through the seal into the bag having an oval shape, the long axis of the oval lying in the longitudinal direction of the seam to be welded. The bag opening is then heat-sealed by means of an impulse band to form the upper weld in the bag, thus achieving a liquid-tight attachment of the connecting member in the bag opening. The connecting member thus communicating with the inside of the bag is shaped at its end protruding from the bag so that it can be detachably joined to a male coupling on the tube 3. Similar connecting members can be provided, as shown in the pressure chamber bag.

As is clear from the drawing, non-return valves may also be arranged in connection with various of the connections. The non-return valves may in this case suitably consist of two flat sheets of polythene welded together to form tubes and secured between the connecting member and the walls of the bag in the seam of the bag so that the lower part of the connecting member protruding into the bag is surrounded by said sheets which form a tube open at the bottom. This non-return valve construction thus permits an unimpeded inflow of liquid or air but prevents any outflow.

As is clear from FIG. 2, the lower end of the pipette 3 protruding into the pressure chamber 2 is provided with a funnel-shaped widening 8a. This widening may of course take some other suitable shape apart from funnel-shape. When the liquid level in the pressure chamber 2 falls as the chamber is emptied, a miniscus forms between the mouth of the pipette and the surface of the liquid and when this is released there is a slight gap between the liquid surface and the mouth of the pipette so that air is rapidly drawn into the pipette and interrupts the syphon action. This action will be considerably more effective if the lower end 8a of the pipette is provided with the widening as shown in FIG. 2.

In the embodiment shown in FIG. 2 the pressure chamber will function so that the total air content in the pressure chamber will be pressed out through the tube 11, whereupon the liquid from the pressure chamber will also be forced up into the tube, but cannot rise higher than the highest point of the pipette. When the syphoning starts and the liquid from the pressure chamber is drawn into the urine bag, the liquid level in the tube 11 will quickly drop and air will be drawn down the tube in to the pressure chamber.

An advantage with the embodiment shown in FIG. 2 is that the space in the pressure chamber when the liquid is emptied from the pressure chamber will not be subjected to partial vacuum, which may happen if the non-return valve mentioned previously, and shown in FIG. 1, sticks, for instance, or fails to function for some other reason.

The invention is not limited to the embodiments shown in the drawings but can be varied in many ways within the scope of the following claims.

The pipette or narrow tube may suitably have an internal diameter of 0.5 to 5 mm, preferably about 2 mm.

I claim:

1. Apparatus for continuously emptying the urine bladder while at the same time training the bladder of an incontinent patient, comprising a pressure chamber locatable below the bladder and having an inlet at its upper end connectable to said bladder, a collecting container connected to said pressure chamber and located below said pressure chamber, the connection between the pressure chamber and the collecting container being formed as a pipette to permit filling of said pressure chamber to a predetermined level, and force the air therein to escape through said inlet to achieve a gradual pressure increase in the bladder resulting in expansion thereof, followed by automatic emptying of bladder and pressure chamber resulting in a contraction of the urine bladder, and uni-directional valve means arranged in association with said pressure chamber to permit air to be introduced therein to equalize the partial vacuum occuring within said chamber after emptying.

2. Apparatus as claimed in claim 1, wherein said inlet is connected to said bladder by a tube and catheter.

3. Apparatus as claimed in claim 2, including an air tube connecting said uni-directional valve to said collecting container.

4. Apparatus as claimed in claim 3 wherein a part of said air tube is higher than the highest part of said pipette.

5. Apparatus as claimed in claim 2 including a closed air container and an air tube connecting said un-directional valve to said closed air container.

6. Apparatus as claimed in claim 5 wherein a part of said air tube is higher than the highest part of said pipette.

7. Apparatus as claimed in claim 1, wherein said pipette extends downwardly into proximity of the bottom of said pressure chamber and is provided with a widened flaring end.

8. Apparatus as claimed in claim 7, wherein said widened end is funnel shaped.

9. Apparatus according to claim 1 wherein at least said pressure chamber is formed with flexible walls responsive to changes in pressure.

10. Apparatus as claimed in claim 1, wherein at least one of said pressure chamber and collecting container comprises a bag of plastic material having sealed edges and at least one integral connecting member communicating for removably securing a connecting tube with the inside of the bag through a sealed edge, the connecting member being of oval cross-section where it passes through said sealed edge and being sealed in said sealed edge and being connected to a tube.

11. Apparatus as claimed in claim 10, wherein the unidirectional valve comprises an open ended tube of flexible material in said bag and surrounding said connecting member, said open ended tube being welded in said sealed edge.

12. The apparatus according to claim 1, wherein said uni-directional valve is connected to the upper part of the urine bag.

13. The apparatus according to claim 1, wherein said pressure chamber, the collecting container and said connection are displaceable arranged in relation to each other.

* * * * *